United States Patent [19]

Alpert

[11] Patent Number: 5,171,149

[45] Date of Patent: Dec. 15, 1992

[54] METHOD AND APPARATUS FOR APPLYING DENTIN CONDITIONING SYSTEM AND DENTAL RESTORATION KIT COMPRISING THE APPARATUS

[75] Inventor: Bruce Alpert, Stamford, Conn.

[73] Assignee: Jeneric/Pentron Incorporated, Wallingford, Conn.

[21] Appl. No.: 706,005

[22] Filed: May 28, 1991

[51] Int. Cl.$^5$ ............................................. A61C 5/00
[52] U.S. Cl. .................................. 433/217.1; 433/80; 401/132
[58] Field of Search ................ 433/90, 80, 216, 217.1, 433/229, 226; 401/132; 604/87; 206/63.5, 368, 369, 528, 219

[56] References Cited

U.S. PATENT DOCUMENTS

| | | | |
|---|---|---|---|
| 1,332,985 | 3/1920 | Jarrett | 401/132 |
| 3,655,035 | 4/1972 | Mühlbauer | 206/47 A |
| 4,294,349 | 10/1981 | Ibsen et al. | 206/63.5 |
| 4,828,113 | 5/1989 | Friedland et al. | 206/570 |
| 4,927,012 | 5/1990 | Rowe | 206/219 |
| 4,941,751 | 7/1990 | Mühlbauer | 366/176 |
| 4,973,248 | 11/1990 | Sigler | 433/90 |

OTHER PUBLICATIONS

Den-Mat "Tenure Dentin Bonding Kit" Advertisement.

Alexander "Precision Applicator and Tandem Droppers" Advertisement.

*Primary Examiner*—Cary E. O'Connor
*Attorney, Agent, or Firm*—Watson, Cole, Grindle & Watson

[57] ABSTRACT

An apparatus for applying a dentin conditioning system to a dentin surface of a tooth comprises a deformable container having a sealed ampule disposed therein, which ampule contains a dentin conditioner. The deformable container is deformed to crush the sealed ampule so that the dentin conditioner may be delivered from the deformable container through a dropper tip. Methods of applying a dentin conditioner are also provided as is a dental restoration kit. Methods and apparatus for simultaneously applying dentin conditioners are also provided.

21 Claims, 2 Drawing Sheets

METHOD AND APPARATUS FOR APPLYING DENTIN CONDITIONING SYSTEM AND DENTAL RESTORATION KIT COMPRISING THE APPARATUS

FIELD OF THE INVENTION

The present invention relates to an apparatus and method for applying a dentin conditioning system in a simple, cost effective manner. More particularly, the present invention relates to a method and apparatus for applying a two component dentin conditioning system, wherein the components are inhibited from contact with each other and oxygen until just prior to use and then are mixed and simultaneously applied to dentin. The dentin conditioner prepares a dentin surface for the application of a powerful adhesive bond layer onto which ceramic crowns, direct composite inlays, orthodontic brackets and other restorative materials may be applied.

BACKGROUND OF THE INVENTION

In order to improve bonding of dental restorations to a tooth surface, particularly dentin, conditioners have been used to prepare the dentin surface for bonding with the restoration. Herein, a dentin conditioning system is one or more dentin conditioners. Dentin conditioning systems have been developed which comprise more than one conditioner. Until now, each has been applied separately. Bonding is fairly easy and routinely achieved on the enamel portion of tooth surfaces, however, the chemical makeup of dentin makes the process of bonding to dentin far more complicated. Dentin conditioning systems which use more than one conditioner improve bonding to dentin through the sequential application of two or more chemical compounds prior to application of an adhesive.

Several conditioning systems which use two or more chemical compounds have been determined to greatly improve the bonding strength of the restoration adhesive to the dentin. However, due to the incompatibility of the different chemical compounds, it has been thought that they must be kept separate and applied separately to the dentin. Additionally, some dentin conditioners become activated or oxidized upon exposure to oxygen. Thus, it is necessary to inhibit the exposure of oxygen to these compounds until the time of use. While the oxidation and/or activation of these compounds usually does not occur immediately upon exposure to oxygen, they are unable to maintain a shelf life in the presence of oxygen which extends much more than a typical business day of a dentist.

Some dentin conditioning systems provide one or more conditioners separately as powders which need be mixed with a solvent. However, since these chemicals in solution are unstable to oxygen exposure, the measuring and mixing must be done by the dentist at chairside just prior to application.

In order to inhibit the exposure of oxygen to a dentin conditioner, methods of packaging the conditioner in a substantially air-tight cartridge have been developed. These cartridges are used in complicated applicator guns and syringes of the types shown in FIG. 1. Loading and unloading of the cartridges within these guns and syringes present a cumbersome task. Also, complicated cartridges are required containing movable rubber stoppers and piercible rubber diaphragms which do not completely inhibit exposure of the cartridge contents to oxygen. An example cartridge is also shown in FIG. 1. The cartridge comprises a glass container 100 in which a single dentin conditioner liquid 101 is disposed. The cartridge has a metal collar 102 at one end which contains a rubber diaphragm 103. At an opposite end of the cartridge is a movable rubber stopper 104 which is moved toward the rubber diaphragm when in use. This forces the conditioner through a hollow needle (not shown) inserted through the diaphragm.

The guns and cartridges are also not completely cost effective. In addition to the complex nature of this applicator system, at least one or more subsequent applications of dentin conditioners are still required in order to complete the conditioning process, a time consuming and sometimes troublesome chore.

The John O. Butler Company of Chicago, Ill. has proposed the use of a crushable glass ampule for the application of a dentin desensitizer, which acts much differently than a dentin conditioner as defined herein. This is a chemical that is applied to exposed dentin to nullify cervical erosion / exposed root surface dentin hypersensitivity thus minimizing pain for up to six months. A single glass ampule is provided in a tube with a swab applicator at one end. The ampule is crushed to allow the tube contents to soak into the cotton swab at the end which is then brushed against the dentin to coat it with the desensitizer.

The present inventor knows of no prior dentin conditioning systems which enable simultaneous application of the conditioners of the system. Instead, the prior systems use sequential application of dentin conditioners when more than one conditioner is used.

SUMMARY OF THE INVENTION

It is an object of the present invention to provide a simple, cost and time efficient method of applying a dentin conditioning system to the dentin surface of a tooth.

It is a further object of the present invention to provide a method and apparatus for applying a dentin conditioner to a dentin surface, wherein the dentin conditioner is inhibited from exposure to oxygen until just prior to use.

It is yet a further object of the present invention to provide a dentin conditioning system and method wherein two or more dentin conditioners are simultaneously applied to dentin in a safe, reliable, single step application.

It is yet a further object of the present invention to provide a disposable dentin conditioning applicator for two or more dentin conditioners which applicator allows storage of the conditioning system for long periods of time by keeping the conditioners separate from each other and inhibiting exposure of oxygen to at least one of the conditioners during periods of storage.

These and other objectives are achieved by the present invention by providing a method and apparatus for storing and applying a dentin conditioning system wherein the conditioner is stored in an air-tight crushable ampule within a deformable container. Upon squeezing the container the ampule is crushed, releasing the conditioner into the applicator from which it can be expelled through a dropper tip either directly onto a dentin surface or into a well for subsequent brushing or sponging application to the dentin. The present invention further provides a conditioning system wherein two or more dentin conditioners are stored in crushable ampules within a frangible container. The ampules are crushed thus permitting mixing of the conditioners just prior to use. Sequential step-wise application of different conditioners is obviated since the conditioners are mixed in the applicator just prior to use and applied simultaneously to the dentin.

The present invention further relates to a dental restoration kit which comprises an applicator as described above for a dentin conditioning system.

The invention may be more fully understood with reference to the accompanying drawings and the following description of the embodiment shown in those drawings. The invention is not limited to the exemplary embodiments but should be recognized as contemplating all modifications within the skill of an ordinary artisan.

DETAILED DESCRIPTION OF THE PREFERRED EMBODIMENTS

Figure 1:
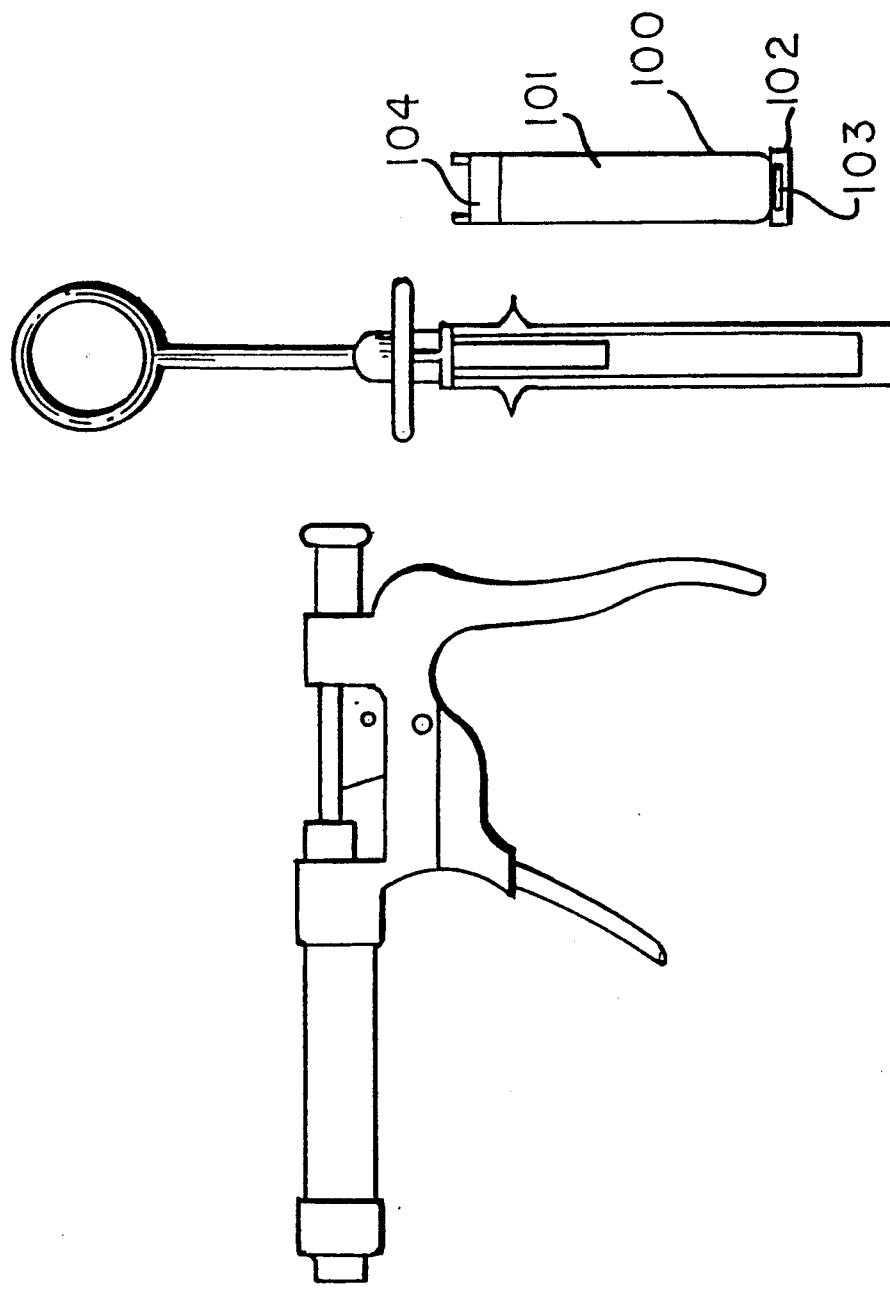
FIG. 1 is a sketch of various prior art applicator systems for single dentin conditioners.
Figure 2:
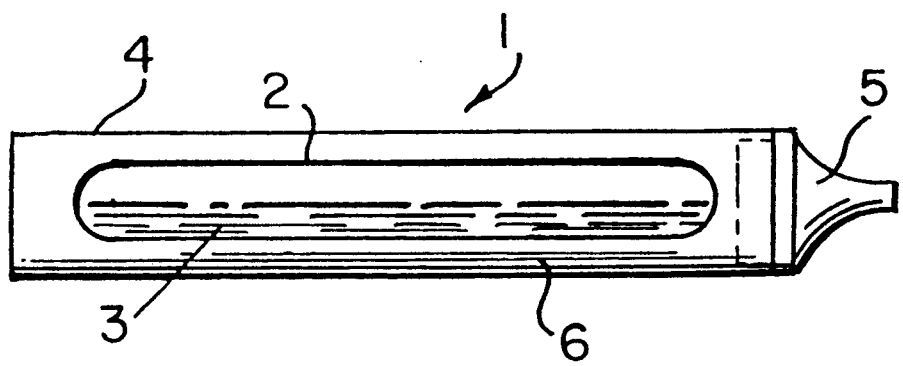
FIG. 2 is a sketch of an embodiment of a dentin conditioning system applicator in accordance with the present invention.
Figure 3:
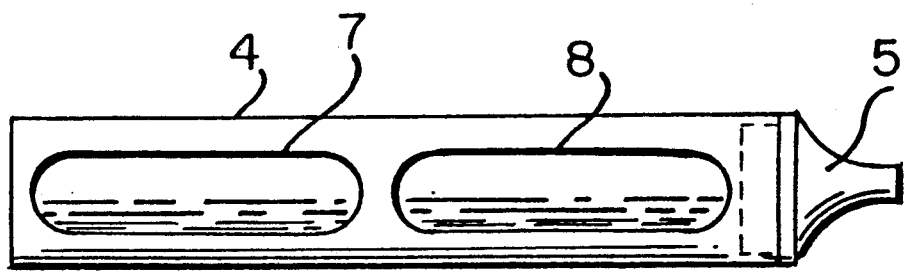
FIG. 3 is another embodiment of an applicator in accordance with the present invention.

FIGS. 2 and 3 show exemplary embodiments of applicators according to the present invention.

In FIG. 2, an applicator 1 is shown which comprises a sealed ampule 2 within a deformable container 4. The container 4 has a dropper tip 5 provided at one end thereof. The dropper tip may be removably insertable into the container to facilitate manufacture of the applicator. An air space 6 may also be provided within the deformable container 4. The container is preferably made of a plastic material which is deformable enough so that when squeezed its side walls can contact side walls of the ampule and exert enough pressure on the ampule to crush it. The container must also be resistant to the conditioners and any solvents that are used. One preferred composition of the containers is a copolymer composition. This releases the conditioner 3 from the ampule into the deformable container where it can be expelled through the dropper tip. The deformable container is resistant to puncture and preferably resistant to scoring, from the broken glass fragments resulting from the crushed ampule.

FIG. 3 shows a similar dentin conditioner applicator in accordance with the present invention, wherein two separate ampules 7 and 8 are provided, each containing a different dentin conditioner. Like the embodiment shown in FIG. 2, the ampules are provided within a deformable container 4 which has a dropper tip 5 at one end thereof.

The ampules may contain just enough conditioner for a single application to the dentin surface of a tooth or they may contain enough conditioner for a dentist to use within the course of a typical business day. Since the conditioners have a short shelf life of up to about 24 hours after mixing and/or exposure to oxygen, aliquots in excess of that which would be used within the shelf life of the conditioner would be wasted. Preferably, only as much conditioner as a dentist would use in a single typical business day is provided within each applicator. Volumes from less than 1/10 of a cubic centimeter to more than a cubic centimeter may be provided within the ampules. In applicators containing two or more ampules, the different conditioners are provided in predetermined proportions, usually in an approximate 1:1 ratio.

The ampules are preferably made of glass and are hermetically sealed after being filled with conditioner and topped with an inert gas. The hermetic sealing of the ampules is important for a number of reasons. Since most of the conditioners used in conjunction with the present invention contain acetone, either as a diluent or a solvent, the hermetic sealing of the conditioner prevents evaporation of this highly volatile liquid. One particularly useful conditioner used in conjunction with the applicators of the present invention is N-phenyl glycine. This conditioner is prepared by mixing the compound in a powdered form with acetone in an inert atmosphere and sealing the mixture within a glass ampule. Since the conditioner and the acetone are premixed, an extra mixing step by the dentist is eliminated. The glycine provides linkages between the dentin and an applied restoration adhesive and also promotes the polymerization of applied resin adhesives. If exposed to oxygen, however, N-phenyl glycine oxidizes which causes it to turn brown and renders it less likely to form polypeptidic bonds.

Another conditioner used in conjunction with the applicators of the present invention is a sodium salt of benzene sulfinic acid. This conditioner is also mixed with acetone and is thus also preferably sealed in an impermeable ampule. The sodium salt of benzene sulfinic acid aids in the adhesion of restoration adhesive to the dentin, and acts as a chealating agent and a polymerization promoter. When benzene sulfinic acid is mixed with N-phenyl glycine, it activates the N-phenyl glycine to a certain extent even in an oxygen inhibited atmosphere. Thus, it is necessary to store these two conditioners in separate ampules during periods of storage. The applicator shown in FIG. 3 is useful for this type of dentin conditioning system.

The applicators of the present invention comprise a dropper tip as shown in FIGS. 2 and 3 which allows a controlled application of the conditioner system to the dentin surface of a patient's tooth. To be most cost effective, the applicator contains enough conditioner for several dentin conditioning applications. If multiple restorations are performed on the same patient, the applicator may be used to directly apply the conditioner through the tip end to the patient's teeth. If, however, different patients having only one or two restorations which require dentin conditioning, then the conditioner system which require dentin conditioning, then the conditioner system may be mixed within the applicator and expelled through the tip end into a well. From the well, the conditioner system may then be applied with a disposable brush or sponge means to ensure a high level of sanitation.

The applicators of the present invention are also useful for many other conditioners currently used in the field of dentistry. Not only conditioners which must be inhibited from exposure to oxygen, but other conditioners may also benefit from the simple, cost-effective storage and delivery devices according to the present invention.

The present invention further relates to a dental restoration kit which comprises a dentin conditioning applicator as described herein. The kit also preferably comprises different shades of dual-cure luting cement, a one-step silane coupler, crown cleaner, etchant, bonding agent, and a complete array of resin stains and opaquers for chair side characterization. Such a kit can be used by a dentist to provide an esthetic, high strength bond in minutes whether bonding all-porcelain restorations or repairing a broken crown. The kit provides the tools needed to prepare a dental restoration in a very short period of time and obviates the needs for sequential, time-consuming separate applications of more than one dentin conditioner.

Methods of applying a dentin conditioner are also provided by the present invention. These methods include providing a dentin conditioner applicator as described above, deforming the deformable container so as to exert enough force on the ampule or ampules to crush the ampule or ampules, mixing the released components if more than one ampule is provided, and dispensing the released conditioner system from the dropper tip of the applicator. In one method according to the present invention, the conditioner system is dispensed directly onto the dentin surface of a tooth. In another method according to the present invention, the conditioning system is dispensed into a well from which it is applied by a brush or sponge means to dentin. Other means of applying the conditioning system dispensed in a well to the dentin surface which are well known to those of skill in the art may also be employed.

Although the present invention has been described in connection with preferred embodiments, it will be appreciated by those skilled in the art that additions, modifications, substitutions and deletions not specifically described may be made without departing from the spirit and scope of the invention defined in the appended claims.

We claim:

1. A method of storing and applying a dentin conditioner which inhibit exposure of the conditioner to oxygen until just prior to application, said method comprising:

hermetically sealing said condition within a crushable ampule;

disposing said ampule within a deformable container, said container having a dropper tip;

deforming said deformable container to exert enough pressure on the sealed ampule to crush the ampule and release the conditioner therefrom; and dispensing said conditioner from said container through the dropper tip onto the dentin surface of a tooth.

2. A method as defined in claim 1, wherein said dispensing step further comprises dispensing said conditioner into a well and applying the conditioner to the dentin with an applicator.

3. A method as defined in claim 2, wherein said applicator comprises a brush means.

4. A method as defined in claim 2, wherein said applicator comprises a sponge means.

5. A method as defined in claim 1, wherein said dentin conditioner comprises at least one member selected from the group consisting of N-phenyl glycine and sodium salts of benzene sulfinic acid.

6. A method of simultaneously applying at least two dentin conditioners to a dentin surface of a tooth, said method comprising:

sealing said at least two dentin conditioners within independent ampules;

disposing said ampules within a deformable container, said container containing a dropper end;

deforming said container so as to exert enough pressure on said ampules disposed in the container to crush said ampules and release said at least two conditioners therefrom;

mixing said at least two conditioners within said deformable container; and simultaneously applying said at least two conditioners to the dentin surface through said dropper tip.

7. A method as defined in claim 6, wherein said simultaneous applying step further comprises delivering said at least two conditioners into a well and applying said at least two conditioners from said well onto the dentin surface with an applicator.

8. A method as defined in claim 7, wherein said applicator comprises a brush means.

9. A method as defined in claim 7, wherein said applicator comprises a sponge means.

10. A method as defined in claim 6, wherein said at least two dentin conditioners comprise N-phenyl glycine and a sodium salt of benzene sulfinic acid.

11. A method of simultaneously applying two dentin conditioners to a dentin surface of a tooth, said method comprising:

disposing at least one of said two dentin conditioners within an ampule and hermetically sealing the ampule so as to inhibit exposure of said at least one dentin conditioner to oxygen;

disposing said at least one sealed ampule within a deformable container and disposing the other of said two dentin conditions within said deformable container;

deforming said deformable container to such an extent that said sealed ampule is broken within the deformable container and the dentin conditioner released from said ampule mixes with the dentin conditioner within said deformable container; and applying said two dentin conditioners simultaneously to said dentin surface.

12. A method as defined in claim 11, wherein said simultaneous applying step further comprises dispensing said at least two dentin conditioners after mixing, within a well and delivering said two dentin conditioners to said dentin surface with an applicator means.

13. A method as defined in claim 12, wherein said applicator means comprises a brush means.

14. A method as defined in claim 12, wherein said applicator comprises a sponge means.

15. A method as defined in claim 11, wherein said two dentin conditioners are N-phenyl glycine and a sodium salt of benzene sulfinic acid.

16. An applicator for storing and applying a dentin conditioner system to a dentin surface, said applicator comprising at least two sealed glass ampules disposed within a deformable container, said container having an opening defining a dropper tip, wherein one of said at least two glass ampules contains N-phenyl glycine and another of said at least two glass ampules contains a sodium salt of benzene sulfinic acid.

17. A dental restoration kit which includes an applicator as defined in claim 16.

18. A dental restoration kit as defined in claim 17, further comprising a bonding agent.

19. A dental restoration kit as defined in claim 17, further comprising luting cement.

20. A kit as defined in claim 19, further comprising a restoration material.

21. A kit as defined in claim 20, further comprising a silane coupler, a cleaner, an etchant, a resin stain, and an opaquer.

* * * * *